United States Patent
Eiling et al.

(12) 
(10) Patent No.: US 6,242,626 B1
(45) Date of Patent: Jun. 5, 2001

(54) BORON-CONTAINING CARBOSILANES, BORON-CONTAINING OLIGO OR POLYCARBOSILAZANES AND SILICON BOROCARBONITRIDE CERAMICS

(75) Inventors: Aloys Eiling, Bochum; Ralf Riedel, Babenhausen; Lutz Ruwisch, Darmstadt, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/402,115

(22) PCT Filed: Mar. 23, 1998

(86) PCT No.: PCT/EP98/01671

§ 371 Date: Sep. 29, 1999

§ 102(e) Date: Sep. 29, 1999

(87) PCT Pub. No.: WO98/45303

PCT Pub. Date: Oct. 15, 1998

(30) Foreign Application Priority Data

Apr. 3, 1997 (DE) ................................. 197 13 767

(51) Int. Cl.[7] .................. C07F 7/08; C07F 7/10; C07F 5/02
(52) U.S. Cl. .......... 556/402; 536/403; 501/96.1; 501/96.3; 501/96.5; 528/30
(58) Field of Search ............... 556/402; 550/403; 501/96.1, 96.3, 96.5; 528/30

(56) References Cited

U.S. PATENT DOCUMENTS

| | | | |
|---|---|---|---|
| 2,831,009 | * 4/1958 | Seyferth | 556/402 |
| 2,902,505 | * 9/1959 | Seyferth | 556/402 |
| 4,851,491 | * 7/1989 | Riccitiello et al. | 556/402 X |
| 5,233,066 | 8/1993 | Jansen et al. | 556/402 |
| 5,312,942 | * 5/1994 | Jansen et al. | 556/402 |
| 5,405,982 | * 4/1995 | Loffelholz et al. | 556/402 X |
| 5,866,705 | * 2/1999 | Jansen et al. | 556/402 |

FOREIGN PATENT DOCUMENTS 4320785   1/1994 (DE).

OTHER PUBLICATIONS

Applied Organometallic Chemistry, vol. 10 (month unavailable) 1996, pp. 241–256 Ralf Riedel, Joachim Bill and Andreas Kienzle, Boron–modified Inorganic Polymers–Precursors for the Synthesis of Multicomponent Ceramics.

Organosilicon Chemistry III, Eds. Auner, Weis, Wiley–VCH (month unavailable) 1998, pp. 629–631, Lutz March Ruwisch, Wolfgang Dressler, Silvia Reichert, Ralf Riedel, Novel Polyorganoborosilazanes for the synthesis of Ultra- –High Thermal Resistant Ceramics.

W. Gerrard, The Organic Chemistry of Boron, Academic Press (month unavailable) 1961, pp. 81, and 152–155, The Attachement of Two Hydrocarbon Groups to Boron.

* cited by examiner

Primary Examiner—Paul F. Shaver
(74) Attorney, Agent, or Firm—Joseph C. Gil; Diderico van Eyl

(57) ABSTRACT

The present invention relates to boron-containing carbosilanes, a process for their preparation, boron-containing oligo- or polycarbosilazanes, a process for their preparation and their use and silicon borocarbonitride ceramics and a process for their preparation.

6 Claims, No Drawings

BORON-CONTAINING CARBOSILANES, BORON-CONTAINING OLIGO OR POLYCARBOSILAZANES AND SILICON BOROCARBONITRIDE CERAMICS

The present invention relates to boron-containing carbosilanes, a process for their preparation, boron-containing oligo- or polycarbosilazanes, a process for their preparation and their use and silicon borocarbonitride ceramics and a process for their preparation.

The process for producing multinary, non-oxidic ceramics via molecular single-component precursors has achieved outstanding importance. It opens up the path to nitridic, carbidic and carbonitridic systems which cannot be prepared by conventional solid-state reactions. The products are distinguished by high purity and a homogeneous element distribution on a molecular level.

Ceramic materials consisting of Si, B, N and C demonstrate particular properties with respect to thermal stability and resistance to oxidation. They can be used industrially as bulk material, in composite materials, but also for coatings or as ceramic fibres. These amorphous boron-containing materials, compared with the boron-free (Si—C—N)-compounds, are distinguished by an increased crystallization inhibition, whereas the carbon-containing compounds have, in addition, higher decomposition temperatures than the carbon-free compounds.

According to U.S. Pat. No. 5,233,066, synthesis of the amorphous ceramics $Si_3B_3N_7$ and $SiBN_3C$ from the precursor trichlorosilylaminodichloroborane (TADB) is achieved by crosslinking with ammonia or amines and subsequent pyrolysis in the gas stream. According to DE-4320785, trissilylalkylboranes of the formula $B[—C_2H_4—SiCl_2X]_3$ are obtained by reacting vinylsilanes of the formula $CH_2=CH—SiCl_2X$ with $BH_3.THF$. Carbon-rich ceramics prepared from this single-component precursor have a (Si:B) ratio of 3:1.

In Organosilicone Chemistry III VCH, (1997), via hydroboration of vinylsilane with $BH_2Cl.SMe_2$, a single-component precursor for Si,B,N,C-containing ceramics, abbreviated hereafter as SiBNC, is described, which has a solid Si:B ratio of 2:1, which is also retained in the ceramics.

In the case of all previously known single-component precursors, thus, disadvantageously, the Si:B ratio is bound to the single-component precursor used and the type of crosslinking The stoichiometry of C:N ratio can only be controlled via the pyrolysis conditions and choice of the crosslinking agent ($NH_3$ or alkylamines).

However, during the pyrolysis, the C:N ratio is set in an uncontrolled manner by reactions which have not been explained in detail. A disadvantage of these syntheses is the low possibility of varying the C content, since extending the side chain does not inevitably lead to a higher C content in the ceramics, but to graphite sediments in the material, which adversely affect the properties.

Although Appl. Organomet. Chem. 10 (1996) 241–256 describes polymeric boron-containing carbosilanes which were obtained by reacting vinyl-containing polysilanes or polysilazanes with borane adducts of the formula $BH_3.SR_2$, this possibility of varying the stoichiometries by using non-single-component precursor compounds, as described in J. Am. Ceram. Soc. 355 (1990) 714–718 for example, leads to ceramics whose properties (e.g. heat stability) are significantly inferior to those produced from single-component precursors.

The object of the present invention was the provision of novel boron-containing carbosilanes which are easy to prepare and permit a high possibility of varying all constituent elements, i.e. B, C, N and Si and can be used as precursors for novel, amorphous silicon borocarbonitride ceramics. For specific applications, by matching the stoichiometry, the respective property optimum is thus to be able to be set.

It has now been found that boron-containing carbosilanes of the formula (I)

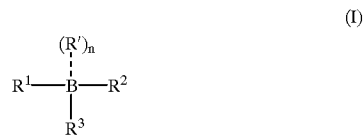

where $R^1=$

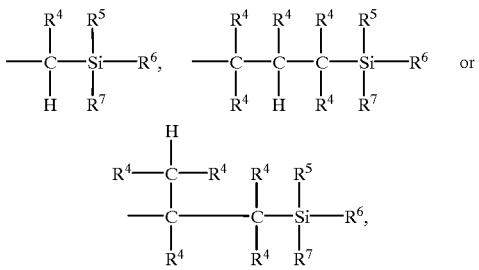

where $R^4=H$, $C_1$–$C_3$-alkyl and/or phenyl, $R^5=Cl$, Br, $R^6$, $R^7=Cl$, Br, H, $C_1$–$C_3$-alkyl or phenyl, $R^2=R^1$ or Cl, Br, $R^3=R^5$, $R'=SMe_2$, $NMe_2H$, where n=0 when $R^2=R^1$, n=1 when $R^2=R^5$ meet the desired profile of requirements.

From these boron-containing carbosilanes of the formula (I) may be prepared carbon-rich ceramics which are distinguished by an elevated stability to alkali metals and alkaline earth metals and their compounds and also by an outstanding resistance to oxidation. In addition, the ceramics of the invention are distinguished by high moduli of elasticity and scratch resistance.

The invention therefore relates to boron-containing carbosilanes of the formula (I)

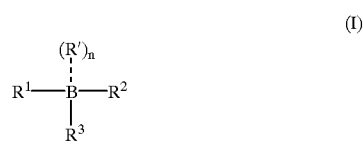

where $R^1=$

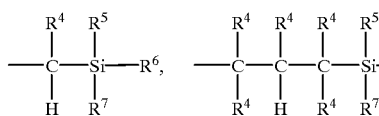 or

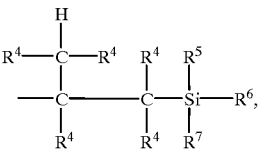

where
$R^4=H$, $C_1$–$C_3$-alkyl and/or phenyl,
$R^5=Cl$, Br
$R^6$, $R^7=Cl$, Br, H, $C_1$–$C_3$-alkyl or phenyl
$R^2=R^1$ or Cl, Br,
$R^3=R^5$,
$R'=SMe_2$, $NMe_2H$
where
$n=0$ when $R^2=R^1$,
$n=1$ when $R^2=R^5$.

In a preferred embodiment of the invention, in the boron-containing carbosilanes of the formula (I)

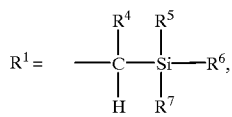

where
$R^4=CH_3$,
$R^5=Cl$ or Me,
$R^6=Me$,
$R^7=R^5$,
and when
$R^2=R^1$,
$R^3$ is Cl,
and when $R^2$ is Cl, $n=1$ and $R'$ is $SMe_2$.

In a further preferred embodiment of the invention, in the boron-containing carbosilanes of the formula (I)

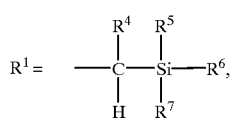

where
$R^4=CH_3$,
$R^5$, $R^6$ and $R^7=Cl$
and when
$R^2=R^1$
$R^3$ is Cl,
and when $R^2$ is Cl, $n=1$ and $R^1$ is $SMe_2$.

The invention additionally relates to a process for preparing the boron-containing carbosilanes of the invention, in which at least one halogenoalkenesilane of the formula (II)

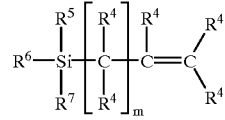
(II)

where
$R^4=H$, $C_1$–$C_3$-alkyl and/or phenyl,
$R^5=Cl$, Br,
$R^6$, $R^7=$independently of one another Cl, Br, H, $C_1$–$C_3$-alkyl or phenyl,
and $m=0$ or 1
is reacted with boranes of the formula (III)

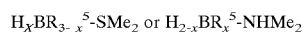

where $x=2$ or 1,
preferably $H_xBR_{3-x}{}^5$-$SMe_2$
where $x=2$,
in an inert gas atmosphere, for example $N_2$, Ar, He,
in an aprotic solvent at temperatures<20° C., preferably 0–10° C.,
in which case the ratio of halogenoalkenesilanes of the formula (II) to boranes of the formula (III) is established by x, that is to say that the compounds of the formulae (II) and (III) are used in accordance with the stoichiometry x.

All of the starting materials coming under the formulae (II) and (III) are commercially available products.

For the purposes of the invention, aprotic solvents are non-halogenated or halogenated aromatic and aliphatic hydrocarbons, preferably toluene, hexane and/or dichloromethane.

In a preferred embodiment of the process of the invention, when $x=1$, the aprotic solvent is halogenated hydrocarbons.

The reaction of the invention is described by way of example with reference to the following diagram:

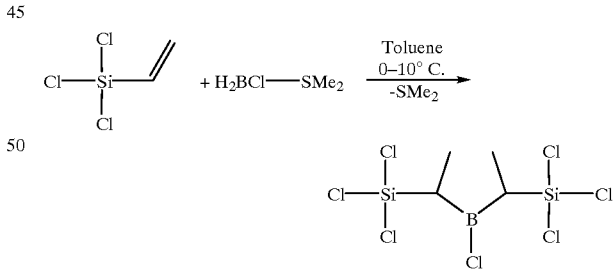

The invention further relates to boron-containing carbosilanes of the formula (IV)

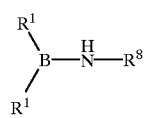
(IV)

where $R^1 =$

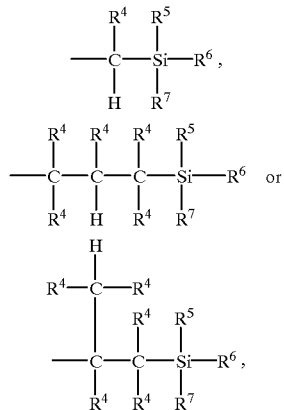

where $R^4 = H$, $C_1$–$C_3$-alkyl and/or phenyl, $R^5 = Cl$, Br, preferably Cl $R^6$, $R^7$ = independently of one another Cl, Br, H, $C_1$–$C_3$-alkyl or phenyl, preferably Cl or methyl and $R^8 = SiR^9$ where $R^9 = C_1$–$C_3$-alkyl or Cl or

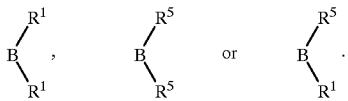

The invention additionally relates to a process for preparing boron-containing carbosilanes of the formula (IV) where $R^8 = SiR^9$ where $R^9 = C_1$–$C_3$-alkyl or Cl, preferably $R^8 = SiCl_3$, according to which at least one boron-containing carbosilane of the formula (I), in which $R^2 = R^1$, and in which $R^6$ and $R^7$ independently of one another are Cl, Br, H, $C_1$–$C_3$-alkyl or phenyl, are reacted in an inert gas atmosphere with $Me_3Si$—NH—$SiCl_3$ at temperatures <70° C., preferably 20 to 40° C.

$Me_3Si$—NH—$SiCl_3$ can be prepared, for example, as described in U.S. Pat. No. 5,233,066.

The reaction of the invention is described by way of example with reference to the diagram below:

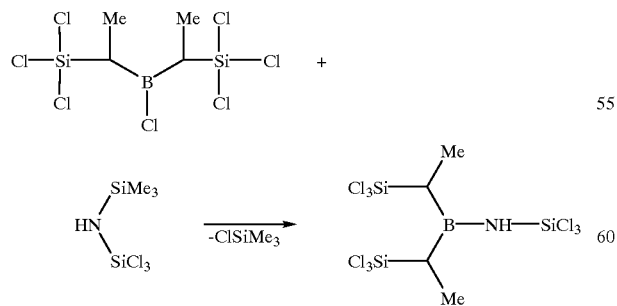

The invention additionally relates to a process for preparing boron-containing carbosilanes of the formula (I) where

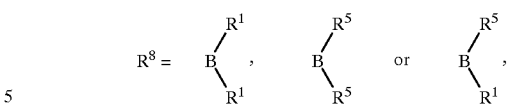

according to which at least one boron-containing carbosilane of the formula (I), in which $R^1 = R^2$, is reacted with $Me_3Si$—NH—$SiMe_3$ at temperatures <70° C., preferably 20 to 40° C., and subsequently thereto the resultant product is reacted either with $BR^{5_3}$ where $R^5 = Cl$, Dr, or $BR^5{}_2R^1$ or with $BR^5(R^1)_2$, preferably $BR^5(R^1)_2$ where $R^5, R^6, R^7 = Cl$, Br.

The reaction of the invention is described by way of example with reference to the diagram below:

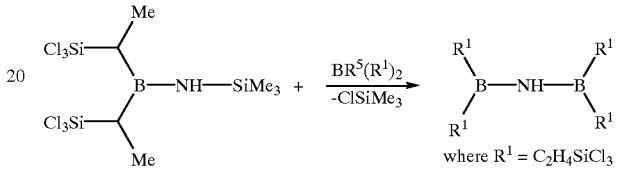

The invention further relates to boron-containing oligo- or polycarbosilazanes obtainable by reacting the boron-containing carbosilanes of the invention with $NH_3$ and/or primary or secondary $C_1$–$C_3$-alkylamines, preferably $MeNH_2$ and/or $Me_2NH$.

The invention further relates to a process for preparing the boron-containing oligo- or polycarbosilazane of the invention, according to which the boron-containing carbosilanes of the formula (I) and/or (IV) are reacted with $NH_3$ and/or with primary or secondary $C_1$–$C_3$-alkylamines, preferably $MeNH_2$ and/or $Me_2NH$.

The process is preferably carried out at temperatures between −70 to −40° C.

To separate off the salt formed in the reaction, such as ammonium hydrochloride or alkylaminehydrochloride, the boron-containing oligo- or polycarbosilazanes can be dissolved in a solvent, particularly preferably in THF, and the salts filtered off.

The invention further relates to silicon borocarbonitride ceramics made from the boron-containing oligo- or polycarbosilazanes of the invention.

The invention further relates to a process for preparing the silicon borocarnonitride ceramics of the invention, according to which the boron-containing oligo- or polycarbosilazane of the invention is pyrolysed in an atmosphere of ammonia or inert gas at temperatures from 25 to 2000° C., preferably 1400–1800° C.

The heating rate in the pyrolysis is preferably 1–100 K/min, particularly preferably 1–20 K/min.

The invention further relates to the use of the boron-containing oligo- or polyborocarbosilazanes of the invention for preparing ceramic powders, ceramic fibres, coatings, composite materials or mouldings.

ILLUSTRATIVE EXAMPLES

Example 1

Preparation of bis[(trichlorosilyl)ethyl]chloroborane 14.6 ml (15.5 g; 0.14 mol) dimethyl sulphide-monochloroborane were added dropwise to a solution of 36 ml (45.6 g; 0.285 mol) of trichlorovinylsilane in 50 ml of toluene with vigorous stirring. The temperature was kept at 10° C. during the addition by ice cooling. The mixture was then kept at this temperature for a further 5 hours and then stirred at room temperature for a further 24 hours. After removing the solvent in vacuo, 35.3 ml (49.0 g; 0.133 mol) of liquid bis[(trichlorosilyl)ethyl]chloroborane were isolated.

Example 2

Reaction of bis[(trichlorosilyl)ethyl]chloroborane with hexamethyldisilazane 10 ml of bis[(trichlorosilyl)ethyl]chloroborane (13.88 g; 37.7 mmol) were added dropwise at 0° C. to 4.0 ml (3.04 g; 18.9 mmol) of hexamethyldisilazane with vigorous stirring. The reaction solution was then stirred for a further 1 h at 40° C. to complete the reaction and resultant trimethylchlorosilane was distilled off 12.9 g (18.9 mmol) corresponding to a quantitative yield, of bis[bis[(trichlorosilyl)ethyl]boryl] amine were obtained.

Example 3

Synthesis of [(dichloromethylsilyl)]ethyldichloroborane-dimethyl sulphide 20 ml (24.44 g; 0.173 mol) of dichloromethylvinylsilane were dissolved in 10 ml of dichloromethane and 20 ml (25.1 g; 0.173 mol) of dimethyl sulphide-dichloroborane were added dropwise at 0° C. with constant stirring. After 5 h at 0° C., the reaction mixture was heated to room temperature and, after a further 24 h, the solvent was removed under reduced pressure. The yield of [(dichloromethylsilyl)]ethyldi-chloroborane-dimethyl sulphide was quantitative.

Example 4

Reaction of [(dichloromethylsilyl)]ethyldichloroborane-dimethyl sulphide with NH$_3$ 32.8 g (0.115 mol) of [(dichloromethylsilyl)]ethyldichloroborane-dimethyl sulphide were added dropwise to 200 ml of condensed ammonia and the reaction mixture was stirred for 1 hour at −60° C. After heating and escape of excess NH$_3$, the product was taken up in tetrahydrofuran and the byproduct NH$_4$Cl was separated off by filtration under protective gas. The solvent was then distilled off and 11.6 g of a whitish-yellow solid, a boron-containing polycarbosilazane having an Si:B ratio of 1:1, were obtained.

Example 5

Pyrolysis of the solid obtained in Example 4.

The solid from Example 4 was added to a quartz Schlenk vessel and heated in argon to 100° C., without the polymer melting in the interim, and kept at this temperature for 1 hour. A black ceramic powder was obtained. The ceramic yield of Si—B—C—N ceramic was 76% by weight.

What is claimed is:

1. A process for preparing a boron-containing carbosilane comprising reacting, in an inert gas atmosphere in an aprotic solvent at a temperature that is <20° C.

(A) at least one halogenoalkenesilane of the formula (II)

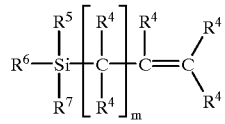

(II)

with (B) boranes of the formula (III)

(III)

wherein the boron-containing carbosilane made with the process has the formula (I)

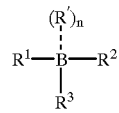

(I)

wherein R$^1$ is

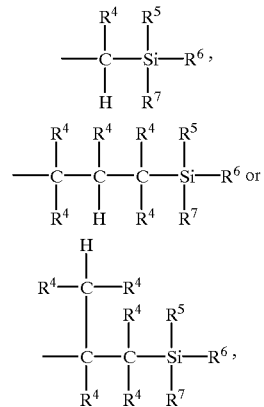

R$^2$ is R$^1$, Cl, or Br,

R$^3$ is R$^5$,

R$^4$ is H, a C$_1$–C$_3$-alkyl or phenyl,

R$^5$ is Cl or Br,

R$^6$, R$^7$, independently of one another, are Cl, Br, H, a C$_1$–C$_3$-alkyl or phenyl, m is 0 or 1 wherein x is 2 or 1 and the ratio of halogenoalkenesilanes of the formula (II) to boranes of the formula (III) is established by x, R' is SMe$_2$ or NMe$_2$H, n is 0 when R$^2$ is R$^1$, and n is 1 when R$^2$ is R$^5$.

2. Process according to claim 1, wherein when x is 1, the aprotic solvent is a halogenated hydrocarbon.

3. A process for preparing a boron-containing carbosilane of the formula (IV)

9

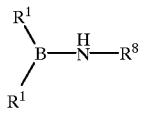
(IV)

comprising reacting
(A) at least one boron-containing carbosilane with
(B) Me$_3$Si—NH—SiCl$_3$ at a temperature that is <70° C.
wherein the at least one boron-containing carbosilane has the formula (I)

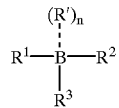
(I)

wherein R$^1$ and R$^2$, independently of one another, are

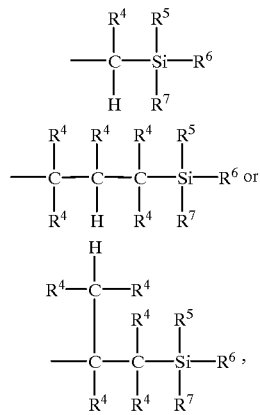

R$^3$ is R$^5$
R$^4$ is H, a C$_1$–C$_3$-alkyl or phenyl,
R$^5$ is Cl or Br,
R$^6$, R$^7$, independently of one another, are Cl, Br, H, a C$_1$–C$_3$-alkyl or phenyl,
R$^8$ is SiR$^9$ or Cl,
R$^9$ is a C$_1$–C$_3$-alkyl,
R' is SMe$_2$ or NMe$_2$H,
wherein n is 0.

4. A process for preparing a boron-containing carbosilane of the formula (IV)

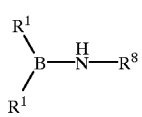
(IV)

comprising reacting
(A) at least one boron-containing carbosilane with
(B) Me$_3$Si—NH—SiMe$_3$ in an inert gas atmosphere at a temperature that is <70° C. and subsequently thereto reacting the resultant product with either BR$^5{}_3$, BR$^5{}_2$R$^1$ or with BR$^5$(R$^1$)$_2$,

10 wherein the boron-containing carbosilane has the formula (I)

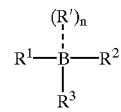
(I)

wherein R$^1$ and R$^2$, independently of one another, are

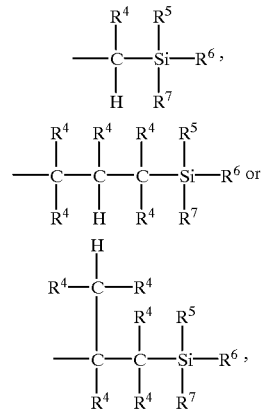

R$^3$ is R$^5$
R$^4$ is H, a C$_1$–C$_3$-alkyl or phenyl,
R$^5$ is Cl or Br,
R$^6$, R$^7$, independently of one another, are Cl, Br, H, a C$_1$–C$_3$-alkyl or phenyl, and
R$^8$ is

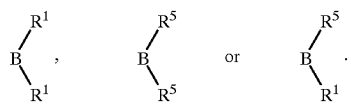

R' is SMe$_2$ or NMe$_2$H, and
n is 0.

5. A process for preparing a silicon borocarbonitride ceramic, comprising pyrolising at least one boron-containing oligo- or polycarbosilazane in an atemosphere of ammonia or inert gas at a temperature that ranges from 25 to 2000° C., wherein the at least one boron-containing oligo- or polycarbosilazane is obtained by reacting
(1) a boron-containing carbosilane with
(2) NH$_3$ and/or primary or secondary C$_1$–C$_3$-alkylamines,
wherein the boron-containing carbosilane has a formula (I)

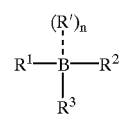
(I)

wherein $R^1$ is selected from the group consisting of

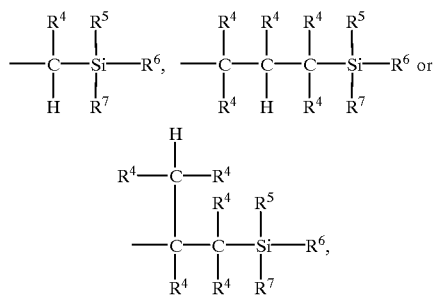

$R^2$ is $R^1$, Cl, or Br,
$R^3$ is $R^5$,
$R^4$ is H, a $C_1$–$C_3$-alkyl or phenyl,
$R^5$ is Cl or Br,
$R^6$, $R^7$, independently of one another, are Cl, Br, H, a $C_1$–$C_3$-alkyl or phenyl,
R' is $SMe_2$ or $NMe_2H$,
n is 0 when $R^2$ is $R^1$, and
n is 1 when $R^2$ is $R^5$.

6. A process for preparing a boron-containing oligo- or polycarbosilazane comprising A) reacting a boron-containing carbosilane of the formula (IV)

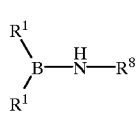

(IV)

with (B) $NH_3$ and/or with primary or secondary $C_1$–$C_3$-alkylamines, wherein the boron-containing oligo- or polycarbosilazane made has the formula (I)

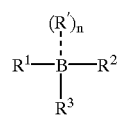

(I)

wherein $R^1$ is

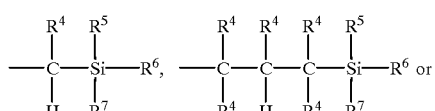
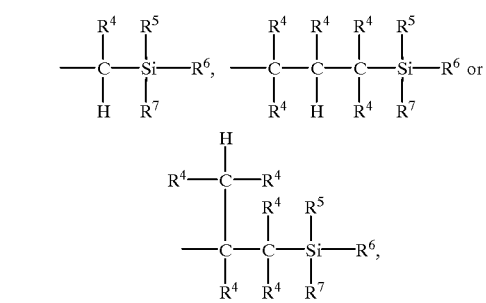

$R^2$ is $R^1$, Cl, or Br,
$R^3$ is $R^5$,
$R^4$ is H, a $C_1$–$C_3$-alkyl or phenyl,
$R^5$ is Cl or Br,
$R^6$, $R^7$, independently of one another, are Cl, Br, H, a $C_1$–$C_3$-alkyl or phenyl,
$R^8$ is $SiR^9$, Cl or

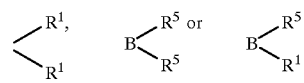

$R^9$ is a $C_1$–$C_3$-alkyl,
R' is $SMe_2$ or $NMe_2H$,
n is 0 when $R^2$ is $R^1$
n is 1 when $R^2$ is $R^5$.

* * * * *